(12) United States Patent
Palmqvist et al.

(10) Patent No.: US 11,154,434 B2
(45) Date of Patent: Oct. 26, 2021

(54) ABSORBENT ARTICLE

(71) Applicant: Essity Hygiene and Health Aktiebolag, Gothenburg (SE)

(72) Inventors: Lisa Palmqvist, Gothenburg (SE); Anna Knös, Gothenburg (SE); Philip Blomström, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 15/734,279

(22) PCT Filed: Jun. 15, 2018

(86) PCT No.: PCT/SE2018/050631
§ 371 (c)(1),
(2) Date: Dec. 2, 2020

(87) PCT Pub. No.: WO2019/240643
PCT Pub. Date: Dec. 19, 2019

(65) Prior Publication Data
US 2021/0212867 A1    Jul. 15, 2021

(51) Int. Cl.
*A61F 13/15* (2006.01)
*A61F 13/511* (2006.01)
(Continued)

(52) U.S. Cl.
CPC .. *A61F 13/51113* (2013.01); *A61F 13/15577* (2013.01); *A61F 13/4751* (2013.01);
(Continued)

(58) Field of Classification Search
CPC .......... A61F 13/51113; A61F 13/15577; A61F 13/4751; A61F 13/49; A61F 2013/4708
See application file for complete search history.

(56) References Cited

U.S. PATENT DOCUMENTS 6,207,738 B1 * 3/2001 Zuckerman ........... F28D 20/023
524/156
6,551,607 B1   4/2003 Minerath, III et al.
(Continued)

FOREIGN PATENT DOCUMENTS

CN    1471595 A    1/2004
CN    1694669 A    11/2005
(Continued)

OTHER PUBLICATIONS

International Preliminary Report on Patentability (Form PCT/IPEA/416) and (Form PCT/IPEA/409) dated Sep. 14, 2020, issued by the European Patent Office, in the corresponding International Application No. PCT/SE2018/050633. (12 pages).
(Continued)

*Primary Examiner* — Jacqueline F Stephens
(74) *Attorney, Agent, or Firm* — Buchanan Ingersoll & Rooney PC

(57) ABSTRACT

An absorbent article including at least a topsheet layer and a backsheet layer, each layer having a body facing surface and a garment facing surface, and longitudinal and transversal edges, the article having a longitudinal front portion, a longitudinal back portion and a crotch portion located between the front and the back portion, the article includes a first zone of microencapsulated phase change material on a surface of a layer of the article, and wherein the first zone has a non-linear boundary in at least the transversal direction of the article.

21 Claims, 3 Drawing Sheets

(51) Int. Cl.
A61F 13/475 (2006.01)
A61F 13/49 (2006.01)
A61F 13/47 (2006.01)

(52) U.S. Cl.
CPC .......... *A61F 13/4758* (2013.01); *A61F 13/49* (2013.01); *A61F 2013/4708* (2013.01)

(56) References Cited

U.S. PATENT DOCUMENTS

| | | | |
|---|---|---|---|
| 10,316,234 | B2 | 6/2019 | Mason |
| 2003/0106605 | A1 | 6/2003 | Jameson et al. |
| 2003/0109816 | A1 | 6/2003 | Lachenbruch et al. |
| 2003/0114812 | A1 | 6/2003 | Braverman et al. |
| 2003/0195448 | A1 | 10/2003 | Jensen |
| 2004/0102750 | A1 | 5/2004 | Jameson |
| 2004/0127872 | A1 | 7/2004 | Petryk et al. |
| 2004/0127883 | A1 | 7/2004 | Cowell et al. |
| 2005/0256478 | A1 | 11/2005 | Genke |
| 2007/0151261 | A1 | 7/2007 | Roberts |
| 2008/0091162 | A1 | 4/2008 | Maldonado et al. |
| 2008/0206529 | A1 | 8/2008 | Ueminami et al. |
| 2008/0208154 | A1 | 8/2008 | Oetjen et al. |
| 2008/0233368 | A1 | 9/2008 | Hartmann et al. |
| 2009/0155325 | A1 | 6/2009 | Wenzel et al. |
| 2009/0288259 | A1 | 11/2009 | Lean et al. |
| 2010/0121304 | A1 | 5/2010 | Zhou et al. |
| 2011/0146900 | A1 | 6/2011 | Ruman |
| 2012/0089106 | A1 | 4/2012 | Komatsu et al. |
| 2012/0193572 | A1 | 8/2012 | MacKay |
| 2012/0242009 | A1 | 9/2012 | Mullane et al. |
| 2013/0261586 | A1 | 10/2013 | Lee et al. |
| 2014/0054827 | A1 | 2/2014 | Mullane et al. |
| 2015/0106992 | A1 | 4/2015 | Blakely et al. |
| 2015/0257943 | A1 | 9/2015 | Noel |
| 2015/0282998 | A1 | 10/2015 | Arizti et al. |
| 2015/0282999 | A1 | 10/2015 | Arizti et al. |
| 2016/0008237 | A1* | 1/2016 | Goldstein ................ A61K 8/40 424/401 |
| 2016/0166074 | A1 | 6/2016 | Rose et al. |
| 2017/0135877 | A1 | 5/2017 | Kudo et al. |
| 2017/0360620 | A1* | 12/2017 | Cree ................ A61F 13/51121 |
| 2018/0140116 | A1 | 5/2018 | Werner |
| 2019/0001017 | A1 | 1/2019 | Palmqvist et al. |
| 2019/0300770 | A1 | 10/2019 | Nomura et al. |

FOREIGN PATENT DOCUMENTS

| | | | |
|---|---|---|---|
| CN | 102827573 | A | 12/2012 |
| CN | 102827582 | A | 12/2012 |
| CN | 103349591 | A | 10/2013 |
| CN | 103374334 | A | 10/2013 |
| CN | 103374335 | A | 10/2013 |
| CN | 103374336 | A | 10/2013 |
| CN | 204379555 | U | 6/2015 |
| CN | 107090075 | A | 8/2017 |
| CN | 107735112 | A | 2/2018 |
| EP | 3162334 | A1 | 5/2017 |
| KR | 20050016837 | A | 2/2005 |
| KR | 20060110492 | A | 10/2006 |
| KR | 20060110495 | A | 10/2006 |
| RU | 2244565 | C2 | 1/2005 |
| RU | 2385168 | C1 | 3/2010 |
| RU | 2540596 | C2 | 2/2015 |
| WO | 0069483 | A1 | 11/2000 |
| WO | 02-24992 | A1 | 3/2002 |
| WO | 2004060244 | A1 | 7/2004 |
| WO | 2007064258 | A1 | 6/2007 |
| WO | 2009105740 | A2 | 8/2009 |
| WO | 2010042470 | A1 | 4/2010 |
| WO | 2011056777 | A1 | 5/2011 |
| WO | 2017002503 | A1 | 1/2017 |
| WO | 2017007398 | A1 | 1/2017 |
| WO | 2017218052 | A1 | 12/2017 |

OTHER PUBLICATIONS

International Search Report (PCT/ISA/210) dated Mar. 15, 2019, by the European Patent Office as the International Searching Authority for International Application No. PCT/SE2018/050630.
International Search Report (PCT/ISA/210) dated Mar. 15, 2019, by the European Patent Office as the International Searching Authority for International Application No. PCT/SE2018/050633.
International Search Report (PCT/ISA/210) dated Mar. 15, 2019, by the Sweden Patent Office as the International Searching Authority for International Application No. PCT/SE2018/050631.
Written Opinion (PCT/ISA/237) dated Mar. 15, 2019, by the European Patent Office as the International Searching Authority for International Application No. PCT/SE2018/050630.
Written Opinion (PCT/ISA/237) dated Mar. 15, 2019, by the European Patent Office as the International Searching Authority for International Application No. PCT/SE2018/050633.
Written Opinion (PCT/ISA/237) dated Mar. 15, 2019, by the Sweden Patent Office as the International Searching Authority for International Application No. PCT/SE2018/050631.
International Preliminary Report on Patentability (Form PCT/IPEA/416 and Form PCT/IPEA/409) dated Aug. 3, 2020, issued by the European Patent Office, in the corresponding International Application No. PCT/SE2018/050630.
Office Action (Rejection) dated Mar. 26, 2021, by the U.S Patent and Trademark Office in corresponding U.S. Appl. No. 15/734,388.
Final Office Action dated Apr. 30, 2021, by the U.S Patent and Trademark Office in corresponding U.S. Appl. No. 15/734,388.
First Office Action dated Apr. 12, 2021, by the Chinese Patent Office in corresponding Chinese Patent Application No. 201880094282.2, and an English Translation of the Office Action. (19 pages).
Office Action (Decision to Grant) dated Jun. 10, 2021, by the Russian Patent Office in Russian Patent Application No. 2021100038, and an English Translation of the Office Action. (19 pages).
Advisory Action dated Jun. 25, 2021, by the U.S. Patent and Trademark Office in co-pending U.S. Appl. No. 15/734,388.
Office Action (Decision to Grant) dated May 24, 2021, by the Russian Patent Office in corresponding Russian Patent Application No. 2021100039, and an English Translation of the Office Action. (18 pages).
Office Action (Question, Arguments, Objection, Proposals) dated May 27, 2021, by the Russian Patent Office in corresponding Russian Patent Application No. 2021100041, and an English Translation of the Office Action. 43 pages).
First Office Action dated Jul. 14, 2021, by the Chinese Patent Office in corresponding Chinese Patent Application No. 201880094215.0, and an English Translation of the Office Action. (15 pages).
Notice of Allowance dated Aug. 13, 2021, by the U.S Patent and Trademark Office in U.S. Appl. No. 15/734,388.

* cited by examiner

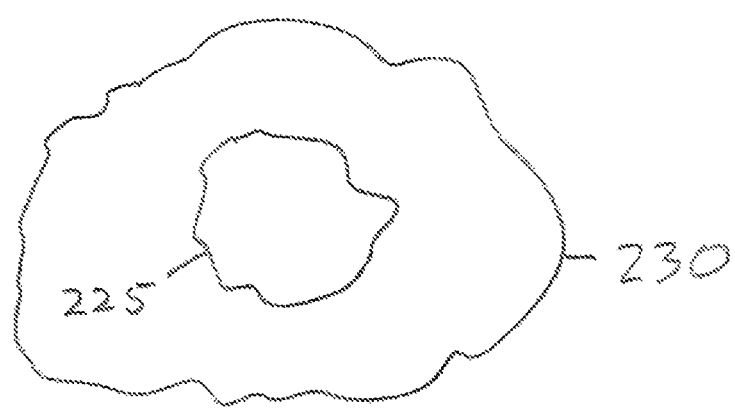

ABSORBENT ARTICLE

TECHNICAL FIELD

The present disclosure pertains to an absorbent article, such as a sanitary napkin, a panty liner, an incontinence pad, an incontinence diaper, a belted diaper, or a baby diaper, comprising a microencapsulated phase change material (PCM). The disclosure further pertains to a method for producing such an absorbent article.

BACKGROUND

Absorbent articles for personal hygiene are designed to absorb and contain body exudates. The absorbent articles normally comprise a topsheet layer facing the user, a backsheet layer facing the garment of a user and optionally an absorbent core located between these layers.

Absorbent articles may contain additives to provide certain advantages for the user. KR20060110492 discloses a diaper comprising microencapsulated phase change material distributed in the absorbent core to suppress a temperature rise of the infant scrotum.

SUMMARY

The present disclosure is based on the insight how an absorbent article may be adapted for specific user requirements to thereby optimize the performance of the article for the user.

Thus, the absorbent article comprises an absorbent article comprising at least a topsheet layer and a backsheet layer, each layer having a body facing surface and a garment facing surface, and longitudinal and transversal edges, the article having a longitudinal front portion, a longitudinal back portion and a crotch portion located between the front and the back portion, the article comprises a first zone of microencapsulated phase change material on a surface of a layer of the article, and wherein the first zone has a non-linear boundary in at least the transversal direction of the article. The disclosure provides for exact placement of the PCM in the absorbent article according to the users requirements and needs.

The zone may be discrete with boundaries starting and ending within the edge borders of the layer. The boundary of the zone may end at least 1 mm from the transversal edges of the layer. The boundary of the zone may end at least 1 mm from the longitudinal edges of the layer. The zone may have a boundary enclosing an area of at least 10 mm$^2$. The non-linear boundary may be obtained by a synchronized in-line printing technique.

The zone may have a rounded shape. The rounded shape of the zone may include a circular shape, an elliptic shape, a rectangular shape and a square shape with rounded corners The first zone may have its center-point in the crotch portion of the article. The article further may comprise a second zone of microencapsulated phase change material on the same surface of the article. The first and second zones may be selected form zones having different microencapsulated phase change materials, different concentrations of a microencapsulated phase change material or comprising microencapsulated phase change material having different phase change temperature intervals.

The phase change material may be a temperature regulating phase change material.

The microcapsules may be of a permanent, non-breakable and non-water-soluble type.

The microencapsulated phase change material may be located on any of the surfaces of the topsheet layer. The article may further comprise an intermediate layer having a body facing surface and a garment facing surface and wherein the microencapsulated phase change material may be located on any of these surfaces.

The article may be selected from a sanitary napkin, a panty liner, an incontinence pad, an incontinence diaper, a belted diaper, and a baby diaper.

The method entails applying PCM to an absorbent article comprising at least a topsheet layer and a backsheet layer, each layer having a body facing surface and a garment facing surface and longitudinal and transversal edges, the article having a longitudinal front portion, a longitudinal back portion and a crotch portion located between the front and the back portion. The method comprising the steps of printing by means of an in-line synchronized print technique a first zone of microencapsulated phase change material on a surface of a layer of the article and wherein the first zone on the article has non-linear boundaries in at least the cross-direction in relation to the production direction. The in-line synchronized print technique may be a flexographic printing technique.

BRIEF DESCRIPTION OF THE DRAWINGS

FIG. 3 is a schematic view of a first zone forming a micropattern within a second zone, wherein the first and the second zone are at least partly overlapping.

DETAILED DESCRIPTION OF THE PREFERRED EMBODIMENTS

Figure 1A:
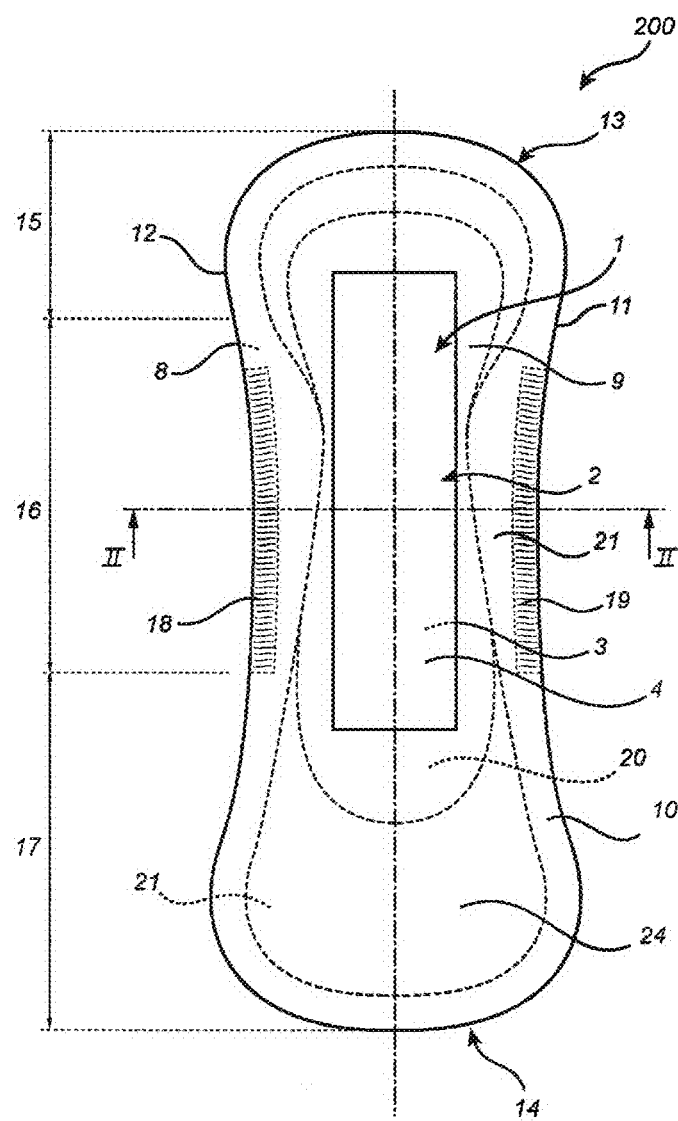
FIG. 1A is a top view of an incontinence pad.

A zone is an area which may the same on every product and thus may be synchronized to the shape of the article. A zone may thus be distinguished from a continuous string, sheet or line in any pattern.

Zones may be functional zones on the product in which the PCM is precisely located through printing to give optimal performance of the additive on the product i.e. where the substance will be most effective e.g. in the most beneficial part of the product.

The zone may be discrete with boundaries starting and ending within the edge borders of the layer. The boundary of the zone may end at least 1 mm from the transversal edges of the layer. The boundary of the zone may end at least 1 mm from the longitudinal edges of the layer.

A first zone 225 may form a micropattern within a second zone 230. A first and a second zone may be at least partly overlapping. There may be a plurality of zones of microencapsulated PCM.

A zone may have a boundary enclosing an area of at least 1 mm$^2$, or at least 5 mm$^2$. The first zone may be more than 0% and less than 100% of the surface area of the layer. The second zone may be more than 0% and less than 100% of the surface area of the layer.

The microencapsulated PCM may be applied on 1-100% of a surface area of a layer of the article, such as 1-90%, such as more than 1% and less than 90%, or more than 1% and less than 80%.

At least the first zone may have a rounded shape. The rounded shape of the zone may include a circular shape, an elliptic shape, a rectangular shape and a square shape with rounded corners. At least the first zone may have its center point in the crotch portion of the article.

The size of the microcapsules may be at least 1 µm, or at least 3 µm, or at least 10 µm and may be below 100 µm, or below 70 µm, or below 30 µm. The size of the microcapsules may be 1-100 µm, or 1-70 µm, or 10-50 µm.

The concentration of microcapsules on the surface of the layer may be at least 0.01 g/m$^2$, or at least 0.05 g/m$^2$ or at least 0.1 g/m$^2$ or at least 0.5 g/m$^2$ and below 17 g/m$^2$, or below 10.0 g/m$^2$ or below 5 g/m$^2$. The concentration of microcapsules on the surface of the layer may be 0.01-17 g/m$^2$, or 0.01-10 g/m$^2$ or 0.01-5 g/m$^2$.

The concentration of PCM in the zones may be >0.01<17 g/m$^2$.

The article may comprise a first and second zone of microencapsulated PCM. The first and second zones may be selected form zones having different microencapsulated phase change materials, different concentrations of a microencapsulated phase change material or comprising microencapsulated phase change material having different phase change temperature intervals, or combinations thereof.

The article may comprise a first and a second zone of microencapsulated phase change material on different layers of the article. The article may comprise a first and a second zone of microencapsulated phase change material on the same surface of a layer of the article. The article may comprise a first and a second zone of microencapsulated PCM on different surfaces of a layer of the article. In an array there may be a first and a second zone of microencapsulated phase change material on different articles.

The concentration of microencapsulated PCM in the first zone may be 0.01-17.0 g/m$^2$. The concentration of microencapsulated PCM in the second zone, if applicable, may be 0.01-17.0 g/m$^2$. The concentration ranges applicable for the first and second zones may be the same. The concentration of the PCM in the absorbent article may differ between the first and second zones within the range 0.01-17.0 g/m$^2$.

The first phase change material may have a phase change transition temperature within 10-50° C., such as 10-40° C. The second zone of microencapsulated phase change material, if applicable, may have a phase change transition temperature within 10-50° C., such as 10-40° C. The temperature ranges applicable for the first and second zones may be the same as disclosed herein, but the individual ranges of the first and second zones may differ between the zones but within this broader range, when applied in the absorbent article.

The capsule material of the microcapsules may be of a non-water-soluble material as known to the skilled man in the art. The capsule material may be of a non-water-soluble polymer material such as polymethyl methacrylate, polystyrene, polyethylene, polyurethane, urea/formaldehyde, melamine/formaldehyde, or inorganic such as calcium carbonate, silica or sodium silicate as known to the man skilled in the art. Natural polymers such as gelatin may also be used as shell materials provided they have low water solubility and melting points above the temperature range of the PCM activity.

The microcapsules may be of a permanent type, i.e. that do not break up during use. Mechanical strength may be important to keep the PCMs intact to avoid leakage and keep the temperature controlling performance. The capsules may need to have sufficient mechanical strength to endure shear forces that may be applied by a moving body during use of the product to avoid leakage of PCM material from the capsules. The urea-formaldehyde system is an example of polymeric shell material that may be tailored to give high shear strength and low leakage. The shell structure is permanent in contrast to capsules for long-lasting or time-release type of claims where the shell should have low enough strength to break upon pressure or friction from the human body to release the core substance. The activation of the microcapsules may be performed by activation upon contact. Not all microcapsules will be activated at the same time as some may be buried further down in the material and there will thus be a slow, continuous and beneficial activation during use of the article. A long-lasting effect can thus be achieved.

The phase change material, i.e. the core material of the microcapsules, may be a reversible temperature regulating phase change material which may revert to its original form. An advantage is the possibility to create an active climate control on demand when needed. In comparison to for example menthol/menthol derivatives which gives a cooling effect regardless of temp, PCM is only cooling at certain temperature ranges and may in addition also emit heat.

Normal skin temperatures are about 31-34° C. for legs and thighs and about 34-37° C. for abdomen. However, in these regions an increased temperature above normal body temperature is also likely to happen when a person moves heavily such as during sports, or is present in a hot environment and in certain climates. Thus, the temperature in different regions of the skin and body differs. For example, the skin in the intimate area closest to the thighs may have a temperature a few degrees higher than that of the skin on the lower thighs due to the enclosed location. Sweat may first increase the temperature and then decrease it when the heat of evaporation makes the sweat fluid cooler. This may be balanced by an area with encapsulated PCM materials. In the center of a hygiene product, where warm fluids such as urine or menstrual blood will warm up and then cool down the product and thus the adjoining skin or membrane, a zone with microencapsulated PCM within a phase change temperature range corresponding to the warm body fluid may be beneficial to balance the temperature variations for increased, more stable, thermal comfort. The waist area of a baby or adult diaper may accommodate warm and humid conditions better if an encapsulated PCM material is added to the waist zone. According to the present disclosure temperature variations may conveniently be alleviated.

The microencapsulated PCM may have a phase change transition temperature to provide a cooling sensation The PCM material for the microcapsules may be a non-volatile organic temperature regulating agent such as paraffin wax mixtures or polymers such as polyethylene glycols, fatty acids or ester derivatives of these (such as caprylic, capric, lauric and tridecylic acid and eutectic mixtures of these with palmitic, myristic or stearic acid) as well as polyalcohols, derivatives thereof and polyethylenes, or they may be an inorganic such as salt hydrates e.g. hydrated calcium and magnesium chlorides or hydrated carbonates. Examples of commercial producers of micro encapsulated PCMs suitable for body wear applications or energy storage applications in the comfort temperature interval for humans are Devan Chemicals (BE), Microtek Laboratories (US), Climator (SE) and MicroCaps (SLO).

Examples of different microencapsulated PCMs to include in the first and second zones, if applicable, are n-alkanes of different chain lengths such as n-octadecane with a phase change temperature interval around 28-32° C. and n-nonadecane with a phase change temperature interval around 32-34° C. Another system may be n-heptadecane, 20-26° C. and n-eicosane, 36-37° C.

The microencapsulated PCM may be printed on a layer of the absorbent article as a composition being a dispersion of the PCM in water or mixed with aqueous binder solution or mixed with a water-based printing ink.

The PCM composition is applied by printing on the absorbent article. By printing we herein mean a precise application of a fluid to form a coating or other dry layer on a substrate. By precise we mean that the medium will be placed in designated zones on the substrate, rather than in a poorly controlled fashion such as when using a spraying, coating or extrusion technique. The print may be of contact type such as selected from flexoprint, screen print, offset, rotogravure or of non-contact type, such as selected from digital inkjet which may be continuous or drop on demand, intermittent drop formation by piezo, heat activated or other type of technology.

The PCM composition may be applied by an in-line synchronized print technique, allowing for an exact placement of the PCM on the article and thereby providing tailor maid solutions for specific needs.

The steps of in-line synchronized printing may be incorporated as steps in a process of manufacturing absorbent articles, or the layers may be in-line synchronized printed before the assembly of the product.

After application of the PCM on the absorbent article it will dry almost instantaneously. However, a drying step may be added, such as blowing hot air on the printed surface.

The PCM composition may be applied in selected areas as desired, and in any desired pattern. The present method allows very accurate zones to be formed.

When arranged in the absorbent article, the top sheet has body facing surface and a garment facing surface. The PCM composition may be applied to one or both of said surfaces. By applying the PCM composition on the body facing surface the user obtains a direct access to the agents. By providing the PCM on a garment facing surface a slower activation and release of the microcapsules are obtained which may be desirable for certain applications. The PCM may also be applied to an intermediate layer of the article. Depending on the location of the PCM various advantageous functional effects can be obtained. Examples of zones of PCM with different functions are given below. These zones can be used individually, but may of course advantageously be combined to achieve the desired characteristics of the absorbent article.

The PCM composition may be applied in a zone along at least a part of the longitudinal side edges. Further, a zone may be applied in a central part of the article.

The microencapsulated PCM may be applied in a zone of the article selected from:
  along longitudinal side edges of the crotch portion;
  a central area of the crotch portion;
  a central area of the front portion;
  a central area of the back portion;
  a waist area.

The absorbent article may further comprise a wing extending from each longitudinal side edge of the article and microencapsulated PCM may be applied in a zone on said wings.

The absorbent article comprises at least a topsheet layer and a backsheet layer and optionally an absorbent layer arranged between the topsheet and the backsheet layers.

Each layer of the absorbent article has a garment facing surface and a body facing surface, and the PCM may be applied to any of said surfaces. The PCM may be added to an intermediate layer, such as an acquisition layer, located beneath a topsheet.

The absorbent article may comprise a liquid pervious body facing topsheet of a nonwoven, a film or a laminate thereof or a foam The backsheet material may be breathable or non-breathable film or nonwoven and film laminate. The back sheet is facing away from the user during use, and is opposite to the body facing topsheet layer of the absorbent article. A fastening means may be applied on the garment facing side of the back sheet, which may be covered by a release paper or single wrap. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment. Furthermore, the fastening means may be a mechanical fastener such as hook-type fasteners, clips, press studs, etc. or may be a frictional fastener such as a frictional coating or open-celled foam. Combinations of different types of fasteners are also conceivable. The fastening means is optional to the invention and may be omitted, if desired.

The absorbent article may comprise a core of absorbent material. The absorbent core may comprise a first and a second absorbent layer. The absorbent layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibers and superabsorbent material, wherein the ratio of superabsorbent material to fibers may vary in the layer. The first and second absorbent layers may have any suitable shape, such as an hourglass shape with widened end portions and a narrow portion in the crotch portion, or a rectangular shape.

The absorbent core may be made up of any suitable absorbent or fluid uptake material as known in the art, such as one or more layers of cellulose fluff pulp, foam, fibre waddings, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. The absorbent core may further incorporate components for improving the properties of the absorbent core. Some examples of such components are binder fibers, fluid-dispersing materials, wetness indicators etc., as known in the art.

The application of the microcapsules by print allows for a precise placement of a delicate printed zone in chosen areas on the article, compared with when the additive is applied for example as a constituent of the spin finish on a topsheet, in a so-called cocktail, which is commonly used by nonwoven suppliers. The in-line positioning (synchronization) of the print enables the print to be placed in exact zones or areas, i.e. particular functional zones of the product. In this way the PCM will be applied only in the printed zones, thus allowing for less amount and possibility for tailor made zones or areas.

Print including one or more of the PCM may be applied in different layers of the product. The topsheet, an intermediate layer, core or acquisition layer, or on a backsheet, glued part, wrap or release paper may be printed. More than one printed area, having the same or different printed additives, are possible on the same layer of the product and on different layers in the product. The printed beneficial zones may be placed within an absorbing area or outside of the absorbing area of an article.

The disclosure will now be described by way of example of an absorbent pad, referring to the drawings.

Figure 1B:
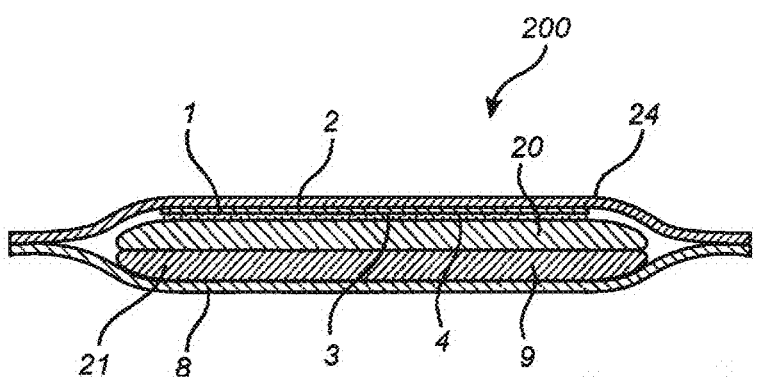
FIG. 1B is a cross-sectional view of the pad in FIG. 1A.

The absorbent article 200 shown in FIGS. 1A and 1B is a urine incontinence protector in the form of a pad. The pad is seen from the side of the pad that is intended to be facing towards a wearer's body when being worn. The pad comprises a liquid permeable topsheet 24, a liquid impermeable backsheet 8, and an absorbent core 9 enclosed between the topsheet 24 and the backsheet 8, and an acquisition and distribution layer 1 arranged between the topsheet 24 and the absorbent core 9.

The topsheet 24 and the backsheet 8 of the pad extend together laterally outside of the absorbent core 9 along the whole circumference of the absorbent core 9 and is connected to each other in an edge joint 10 around the periphery of the absorbent core 9. The topsheet 24 comprises any material which is suitable for the purpose, i.e. soft and liquid pervious.

The backsheet 8 is fluid impermeable. However, backsheet materials that are only fluid repellant may be used particularly in instances where relatively small amounts of urine are expected to be taken up. Furthermore, the backsheet 8 may have an outer, garment-facing surface of a textile material such as nonwoven.

The absorbent core 9 may be made up of any suitable absorbent or fluid uptake material as known in the art, such as one or more layers of cellulose fluff pulp combined with fibers or particles of highly absorbent polymer material.

The pad in FIG. 1A has an elongate, generally rectangular shape when fully extended in all directions. Any suitable shape may be used for the absorbent product, such as hourglass shape, trapezoidal shape, triangular shape an oval shape, etc. The shape of the product of the invention may be symmetrical about a transverse center line through the product, or may be asymmetrical with end portions having differing shapes and/or differing sizes. The pad has two longitudinal side edges 11, 12 extending generally in the same direction as a longitudinal center line through the absorbent product. Front and rear end edges 13, 14 typically extend transversely to the longitudinal center line at the ends of the absorbent product. The rear end edge 14 is intended to be orientated rearwards during use of the absorbent article, and the front-end edge 13 is intended to be facing forwards towards the abdomen of the wearer. The pad has a longitudinal front portion 15, a longitudinal back portion 17 and a crotch portion 16 located intermediate the front and back portions 15, 17. The crotch portion 16 is a portion which is intended to be placed against the crotch of a wearer during use of the product and to constitute the main acquisition area for body fluid that reaches the pad. The pad may further include fastening means for fastening of the absorbent product inside a supporting pant garment, such as a pair of underpants.

Elastic elements 18, 19 may be arranged along the side edges laterally outside the absorbent core 8. The elastic elements 18, 19 may be bands of elastic material. The elastic elements 18, 19 are optional components of the absorbent product and may be omitted.

The acquisition and distribution material 1 in FIG. 1A is situated above the absorbent core 9 and beneath and in direct contact with the topsheet 24 and may be a nonwoven high loft material or a perforated material such as a SMS material.

The absorbent core 9 in FIG. 1A has a first absorbent layer 20 and a second absorbent layer 21. The second absorbent layer 21 is placed below the first absorbent layer 20. The first absorbent layer 20 is smaller than the second absorbent layer 21. The second absorbent layer 21 extends further forward and rearward in the absorbent product than the first absorbent layer 20.

However, the absorbent core may also comprise only one single layer or may comprise one or more further absorbent layers. The size of the different layers may also vary, and the absorbent core 9 described in FIGS. 1A and 1B is only one illustration of an absorbent core.

In FIG. 1B a cross-sectional view of the absorbent pad of FIG. 1A is shown, along the line II-II. The pad has a liquid permeable top sheet 24, a liquid impermeable back sheet 8, and an absorbent core 9 enclosed between the top sheet 24 and the back sheet 8 and an acquisition and distribution material 1 is located between the topsheet 24 and the absorbent core 9.

EXAMPLE 1

Figure 2:
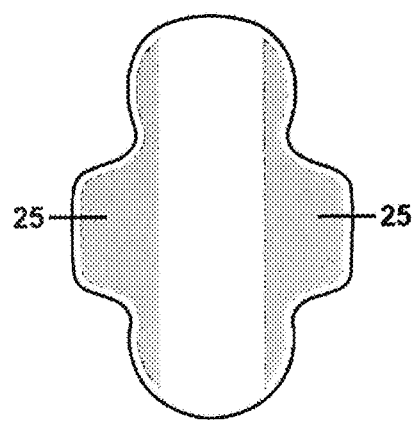
FIG. 2 is a top view of a pad with PCM zones.

A feminine pad was produced having zones according to area 25 in FIG. 2, by in line flexographic printing of microencapsulated PCM on a material for an incontinence pad, on the left and right-hand side of the center line in the longitudinal direction. The outer side of the zone follows the outer contour of the product but also the area being folded around the underwear to create a good comfort against the skin. A small portion, 3 mm wide, of the outermost area on the pad is not covered by the PCM. The PCM material was MPCM32 wet cake, Microtek laboratories (temp interval 30-35° C.) and the concentration was 1.8 g/m$^2$.

The invention claimed is:

1. An absorbent article comprising at least a topsheet layer and a backsheet layer,
   each layer having a body facing surface and a garment facing surface, and longitudinal and transversal edges,
   the article having a longitudinal front portion, a longitudinal back portion and a crotch portion located between the front and the back portion,
   the article comprises a first zone of microencapsulated temperature-regulating phase change material on a surface of at least one of the layers of the article,
   wherein the microcapsules are of a permanent, non-breakable and a non-water-soluble type, and
   wherein the first zone is discrete with boundaries starting and ending within an edge border of the at least one layer, and
   wherein the first zone has a non-linear boundary in at least the transversal direction of the article.

2. The absorbent article according to claim 1, wherein the boundary of the zone ends at least 1 mm from the transversal edges of the layer.

3. The absorbent article according to claim 1, wherein the boundary of the zone ends at least 1 mm from the longitudinal edges of the layer.

4. The absorbent article according to claim 1, wherein the zone has a boundary enclosing an area of at least 10 mm$^2$.

5. The absorbent article according to claim 1, wherein the zone has a rounded shape.

6. The absorbent article according to claim 5, wherein the rounded shape of the zone includes a circular shape, an elliptic shape, a rectangular shape, and a square shape with rounded corners.

7. The absorbent article according to claim 1, wherein the zone has its center point in a crotch portion of the article.

8. The absorbent article according to claim 1, wherein the non-linear boundary is obtained by a synchronized in-line printing technique.

9. The absorbent article according to claim 1, wherein the article further comprises a second zone of microencapsulated phase change material on the same surface of the article.

10. The absorbent article according to claim 9, wherein the first and second zones are selected form zones having different microencapsulated phase change materials, different concentrations of a microencapsulated phase change material or comprising microencapsulated phase change material having different phase change temperature intervals.

11. The absorbent article according to claim 9, wherein the first zone is more than 0% and less than 100% of the surface area of the layer.

12. The absorbent article according to claim 9, wherein the second zone is more than 0% and less than 100% of the surface area of the layer.

13. The absorbent article according to claim 9, wherein the first phase change material has a phase change transition temperature within 10-50° C.

14. The absorbent article according to claim 9, wherein the second zone of microencapsulated phase change material has a phase change transition temperature within 10-50° C.

15. The absorbent article according to claim 9, wherein the first and second zones are at least partly overlapping.

16. The absorbent article according to claim 9, wherein the second zone forms a micropattern within at least a part of the first zone.

17. The absorbent article according to claim 1, comprising a plurality of zones of microencapsulated PCM.

18. The absorbent article according to claim 1, wherein the microencapsulated phase change material is located on any of the surfaces of the topsheet layer.

19. The absorbent article according to claim 1, wherein the article is selected from a sanitary napkin, a panty liner, an incontinence pad, an incontinence diaper, a belted diaper, and a baby diaper.

20. A method of applying PCM to an absorbent article comprising at least a topsheet layer and a backsheet layer, each layer having a body facing surface and a garment facing surface and longitudinal and transversal edges, the article having a longitudinal front portion, a longitudinal back portion and a crotch portion located between the front and the back portion, comprising the steps of:
   printing by means of an in-line synchronized print technique a first zone of microencapsulated temperature-regulating phase change material on a surface of at least one of the layers of the article,
   wherein the microcapsules are of a permanent, non-breakable and non-water-soluble type, and wherein the first zone on the article is discrete with boundaries starting and ending within an edge border of the at least one layer, and wherein the first zone has non-linear boundaries in at least the cross-direction in relation to the production direction.

21. The method of applying PCM according to claim 20, wherein the in-line synchronized print technique is a flexographic printing technique.

* * * * *